United States Patent
Iaia

(10) Patent No.: US 6,702,823 B2
(45) Date of Patent: Mar. 9, 2004

(54) DEVICE FOR IDENTIFYING THE POSITION OF INTRAMEDULLARY NAIL SECUREMENT SCREW HOLES

(75) Inventor: Ciro Rosario Iaia, Rimini (IT)

(73) Assignee: Hit Medica S.r.l., Rimini (IT)

( * ) Notice: Subject to any disclaimer, the term of this patent is extended or adjusted under 35 U.S.C. 154(b) by 29 days.

(21) Appl. No.: 10/043,307

(22) Filed: Jan. 14, 2002

(65) Prior Publication Data

US 2002/0058949 A1 May 16, 2002

(51) Int. Cl.[7] .................. A61B 17/56; A61B 17/58; A61B 17/60; A61F 2/00; A61F 2/32
(52) U.S. Cl. ........................... 606/98; 606/67
(58) Field of Search .................. 606/60, 62, 64, 606/65, 66, 67, 96, 97, 98

(56) References Cited

U.S. PATENT DOCUMENTS

| | | | | |
|---|---|---|---|---|
| 4,441,492 A | * | 4/1984 | Rydell et al. | 128/92 |
| 4,622,959 A | * | 11/1986 | Marcus | 128/92 |
| 4,667,664 A | | 5/1987 | Taylor et al. | |
| 5,100,404 A | * | 3/1992 | Hayes | 606/62 |
| 5,207,682 A | * | 5/1993 | Cripe | 606/96 |
| 5,474,561 A | * | 12/1995 | Yao | 606/98 |
| 6,053,918 A | * | 4/2000 | Spievack | 606/64 |
| 6,379,360 B1 | * | 4/2002 | Ackeret et al. | 606/67 |
| 2002/0151897 A1 | * | 10/2002 | Zirkle, Jr. | 606/62 |
| 2003/0069581 A1 | * | 4/2003 | Stinson et al. | 606/62 |

FOREIGN PATENT DOCUMENTS

| | | | |
|---|---|---|---|
| EP | 1 099 413 | 5/2001 | |
| FR | 2 716 615 | 9/1995 | |
| IT | BO2000000066 U | 5/2000 | |
| WO | 92 01422 | 2/1992 | |
| WO | WO 96/03085 | * 8/1996 | A61B/17/17 |

* cited by examiner

Primary Examiner—Eduardo C. Robert
Assistant Examiner—Anuradha Ramana
(74) Attorney, Agent, or Firm—Guido Modiano; Albert Josif; Daniel O'Byrne

(57) ABSTRACT

A device for identifying the position of the distal holes for passage of securement screws provided in an intramedullary nail inserted in a medullary canal of a long bone, having an arm that protrudes from said medullary canal, provided with a fixing element for rotational and axial fixing to the end of said nail, the arm comprising a portion that protrudes outside the bone provided with elements for the coupling, at a selective distance, of a hollow stem which encloses a plurality of channels allowing sliding therein of guiding wires for guiding a cannulated bone drilling tool and at least one securement screw to be inserted after removal of the cannulated tool through the bone and distal holes of the intramedullary nail.

9 Claims, 3 Drawing Sheets

DEVICE FOR IDENTIFYING THE POSITION OF INTRAMEDULLARY NAIL SECUREMENT SCREW HOLES

BACKGROUND OF THE INVENTION

The present invention relates to a device for identifying the position of the securement screws of an intramedullary nail, particularly the distal screws.

Devices of the indicated type are already known from patents FR 2705558, U.S. Pat. No. 4,733,654, WO 92/01422, relating to intramedullary nails which are inserted in the medullary canal of a long bone and are fixed at their opposite ends by means of through screws.

While fixing the screws to the insertion end of the nail does not entail particular problems, fixing the screws at the opposite end is often critical, owing to the fact that the nail, during insertion, is subjected to torsions and deformations that produce a misalignment of the position of the screw passage holes that cannot be ascertained from outside.

SUMMARY OF THE INVENTION

The aim of the present invention is therefore to provide a device that allows to identify the position of the screw passage holes after the intramedullary nail has been inserted in the bone.

Within this aim, an object of the present invention is to provide a device that allows quick identification of the position of the screws, so as to reduce surgery times and exposure of the surgeon and patient to the radiation of exploratory X-rays.

Another object of the present invention is to provide a structure that is simple, relatively easy to provide in practice, safe in use, effective in operation, and relatively low in cost.

This aim and these and other objects which will become better apparent hereinafter are achieved by the present device for identifying the position of the distal holes for the passage of securement screws provided in an intramedullary nail inserted in the medullary canal of a long bone characterized in that it comprises an arm provided with means for rotational and axial fixing to the end of said nail that protrudes from said medullary canal, said arm comprising a portion that protrudes outside said bone and is provided with means for the coupling, at a selective distance, of a hollow stem which encloses a plurality of channels that allow the sliding therein of guiding wires for a cannulated tool for drilling said bone and for at least one of said securement screws to be inserted after removing said cannulated tool through said bone and said distal holes of said intramedullary nail.

BRIEF DESCRIPTION OF THE DRAWINGS

Further characteristics and advantages of the present invention will become better apparent from the detailed description of a preferred but not exclusive embodiment of a device for identifying the position of the securement screws of an intramedullary nail, illustrated only by way of nonlimitative example in the accompanying drawings, wherein.

DESCRIPTION OF THE PREFERRED EMBODIMENTS

Figure 1:
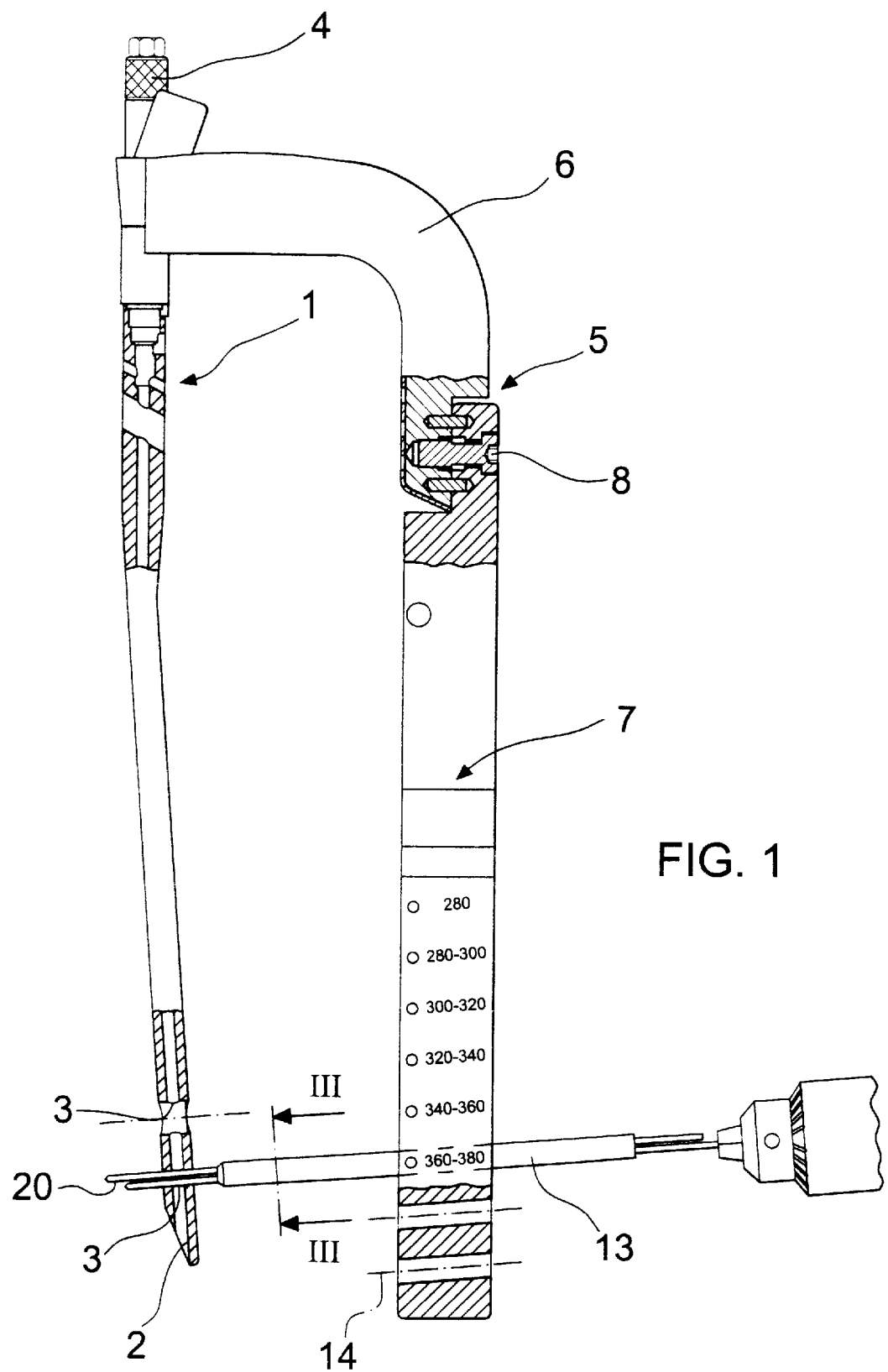
FIG. 1 is a front view of the device according to the invention.

With reference to the figures, the reference numeral 1 designates a generic intramedullary nail, which has, at one end, a tip 2, by means of which it is inserted in the medullary canal of a long bone (for example the femur, tibia, etcetera); proximate to said tip usually two distal through holes 3 are provided, which have parallel axes, for corresponding distal screws for the securement of said nail.

The end of the nail 1 that lies opposite the tip 2 and protrudes from the medullar canal is provided with fixing means 4, by way of which it is fixed, both axially and rotationally, to a securement device, generally designated by the reference numeral 5. For the sake of brevity in description, the fixing means are not described in detail hereinafter, since they are not the subject of the present invention.

The securement device 5 comprises an arm 6 for supporting the means 4 for fixing the intramedullary nail 1; said arm is curved substantially at right angles and is connected to a portion 7, which lies outside the bone and the muscle tissues that cover it.

Figure 2A:
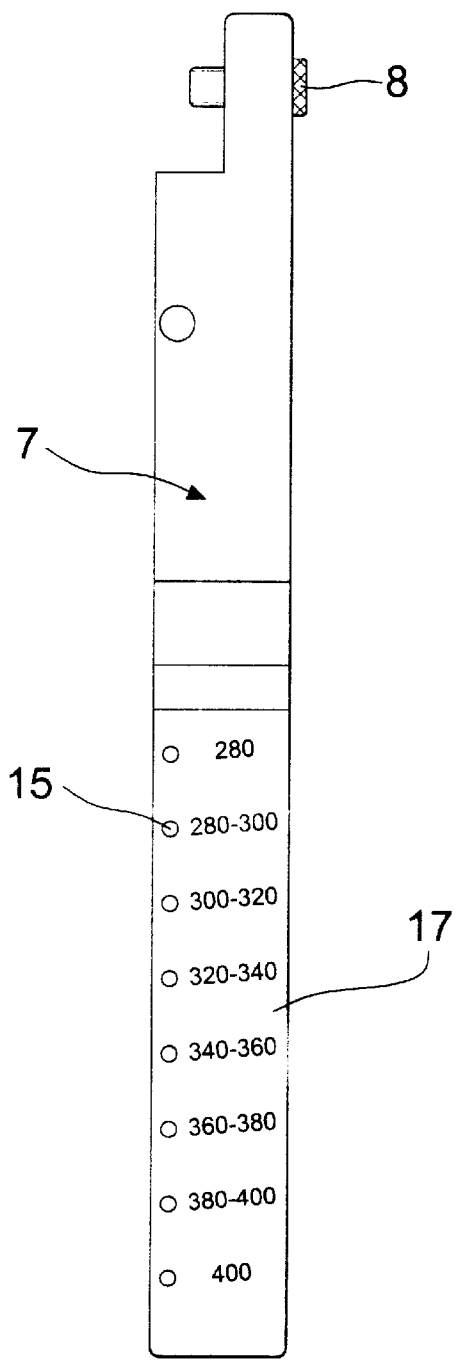
FIGS. 2a and 2b are a front and a side elevation view, respectively of the portion of said device that lies outside the bone.
Figure 2B:
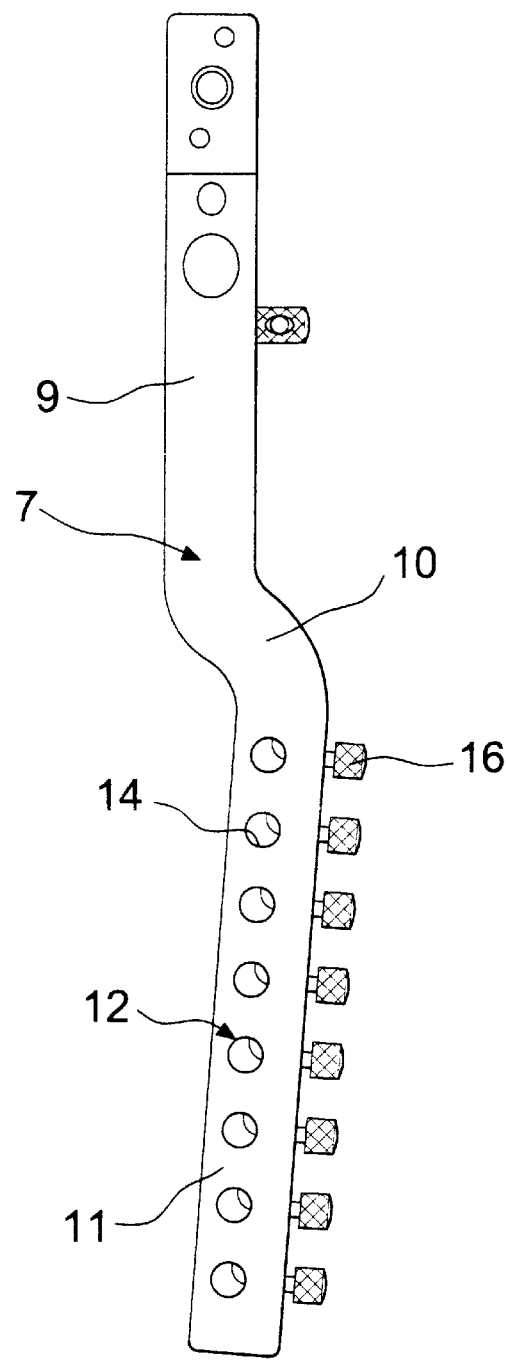

The portion 7 (FIG. 2) has an upper end, which is provided with elements 8 for connection to the arm 6, and has a straight upper part 9, which is substantially parallel to the nail and is continued by an intermediate portion 10, which is substantially S-shaped, and by a straight lower portion 11, which is substantially parallel to the nail 1. In this manner, the parts 9, 10 and 11 form a profile that essentially duplicates the anatomical profile of the bone being treated.

The lower part 11 of the portion 7 is provided with means 12 for coupling, at a selective distance, a hollow stem 13, which is suitable to identify the position of the distal holes 3 in the intramedullary nail. The coupling means 12 are constituted by a plurality of through holes 14, which are distributed preferably equidistantly along the lower part 11 of the portion 7; said through holes 14 have axes that are substantially parallel to the axes of the distal holes 3 and are affected at right angles by respective female threads 15 for grub screws 16 for fixing the hollow stem 13.

The through holes 14 bear, along the lower part 11 of the portion 7, respective anthropometric reference markings 17, which indicate the correct position for placing the distal screw in relation to the length of the nail.

The stem 13 can be orientated with respect to the portion 7 in order to achieve alignment with the corresponding distal hole 3 by adjusting the position of the grub screw 16 engaged with the surface of said stem 13.

Figure 3:
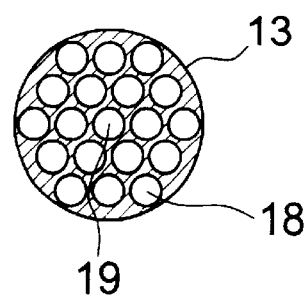
FIG. 3 is a transverse sectional view, taken along the line III—III of FIG. 1, of the hollow stem of the device according to the invention.

The hollow stem 13 comprises, inside it, a plurality of channels 18, which have a circular cross-section (FIG. 3) and are arranged in a bundle so as to have mutually parallel axes or, as an alternative, so that their axes substantially converge. The channels are distributed concentrically with respect to a central channel 19 and their diameter is such as to allow the sliding, inside them, of guiding wires 20 for a cannulated drilling tool or cannulated screw.

The method for using the described device is entirely self-evident.

After inserting the nail 1 in the medullar canal of the bone and applying the securement device 5, locking it to the top of the nail with the fixing means 4, the through holes 14 into which the hollow stem 13 is to be inserted, after providing an initial perforation of the cortex with appropriate instruments, are identified with reference to the corresponding anthropometric marking 17 and to the size of the nail 1.

Figure 4A:
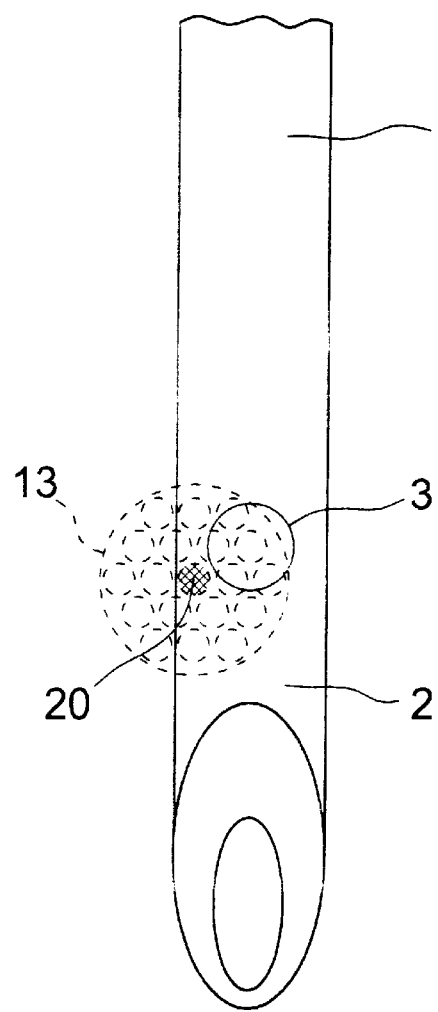
FIGS. 4a and 4b are detail views of the sequence for positioning the guiding wires through the intramedullary nail.
Figure 4B:
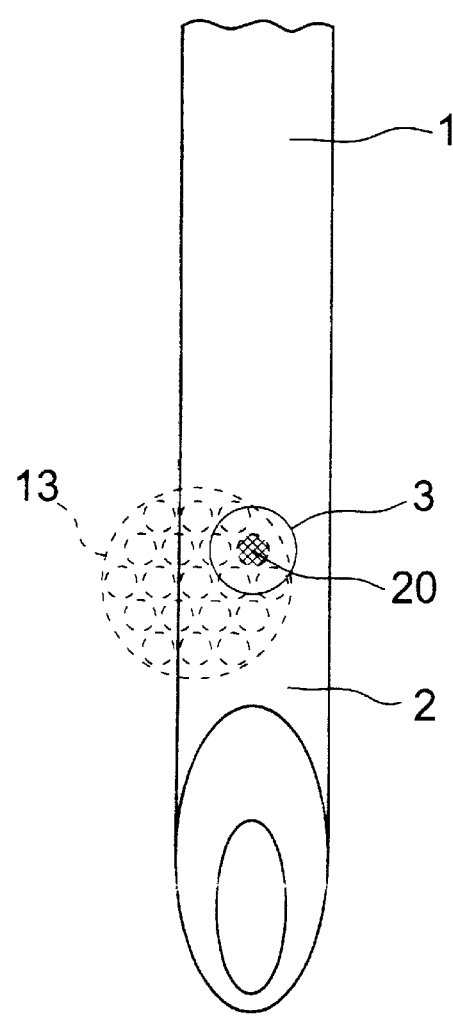

Following insertion of the hollow stem 13 in the selected through hole 14 so that said stem is substantially orientated and aligned with the axis of the corresponding distal hole 3 of the nail 1, a first guiding wire 20 is inserted through the central channel 19 of said stem (see FIG. 4 in this regard) in order to try to locate the center of the corresponding distal hole 3 of the nail 1.

By performing a test with an image intensifier, it is possible to determine the position of the first guiding wire 20 with respect to the distal hole 3 of the nail 1; if the first guiding wire 20 is not positioned correctly, another guiding wire is inserted, using one of the remaining channels 18 whose axis is proximate to the axis of the distal hole 3, until the optimum alignment position is determined.

After removing the hollow stem 13 from the through hole 14 in which it is inserted and fixed, while leaving the guiding wire 20 in the bone, the bone is drilled by means of a cannulated tool that can slide along the guiding wire 20; this is followed by the fixing of the nail, for example by means of one or two solid or cannulated screws, in the respective distal holes 3, to be guided in the same manner along said guiding wire.

It is evident that the invention perfectly achieves the intended aim and objects.

A considerable advantage offered by the device is that it allows to shorten surgery times and most of all to reduce the exposure of surgeon and patient to the radiation of exploratory X-rays during operations.

The invention thus conceived is susceptible of numerous modifications and variations, all of which are within the scope of the appended claims.

All the details may further be replaced with other technically equivalent ones.

In practice, the materials used, as well as the shapes and the dimensions, may be any according to requirements without thereby abandoning the scope of the protection of the appended claims.

What is claimed is:

1. A device for identifying the position of distal holes for passage of securement screws provided in an intramedullary nail inserted in a medullary canal of a long bone, comprising: an arm; fixing means provided at said arm for rotational and axial fixing thereof to an end of the nail that protrudes from the medullary canal, said arm comprising a portion that protrudes outside the bone; a hollow stem which encloses a plurality of channels, said plurality of channels of said hollow stem being arranged in a configuration grouped in a bundle and comprising a central channel surrounded by concentric channels distributed about a plurality of radiuses; a cannulated tool for drilling said bone; coupling means provided at said arm portion for coupling thereat, at selectable distances, said hollow stem; and guiding wires for guiding said cannulated tool and at least one securement screw to be inserted through said bone and said distal holes of said intramedullary nail after removal of said cannulated tool.

2. The device of claim 1, wherein said arm portion has a profile shape corresponding to an anatomical profile of the bone and comprises a substantially straight upper part, which is parallel to said nail, an intermediate part, which is substantially S-shaped, and a substantially straight lower part, which is parallel to said nail.

3. The device of claim 2, wherein said coupling means comprises a plurality of through holes, which are distributed preferably equidistantly along said lower part of said arm portion.

4. The device of claim 3, wherein said through holes have respective axes which are substantially parallel to respective axes of said distal holes of said intramedullary nail.

5. The device of claim 4, wherein said hollow stem is angularly, selectively positionable in one of said through holes of said arm portion.

6. The device of claim 4, wherein said through holes are provided, along said lower part of said arm portion, with respective anthropometric reference markings.

7. The device of claim 1, wherein said plurality of channels of said hollow stem are arranged with axes thereof being substantially parallel.

8. The device of claim 1, wherein said plurality of channels of said hollow stem are arranged with axes thereof being substantially convergent.

9. The device of claim 1, wherein said at least one securement screw is of a cannulated type.

* * * * *